United States Patent [19]

Appelgren et al.

[11] Patent Number: 4,968,506

[45] Date of Patent: Nov. 6, 1990

[54] PHARMACEUTICAL DOSAGE WITH CORE OF N-ACETYL CYSTEIN

[75] Inventors: Curt H. Appelgren, Kungsbacka; Eva C. Eskilsson, Mölnlycke; Ulf G. Smith, Kungsbacka, all of Sweden

[73] Assignee: Lejus Medical Aktienbolag, Mölndal, Sweden

[21] Appl. No.: 258,255

[22] Filed: Oct. 14, 1988

[30] Foreign Application Priority Data

Oct. 10, 1988 [SE] Sweden .................. 8803583

[51] Int. Cl.⁵ .............................................. A61K 9/52
[52] U.S. Cl. .................................. 424/456; 424/476; 424/480; 424/481; 424/482; 424/494; 424/496; 424/497; 424/498
[58] Field of Search ............ 424/479, 480, 481, 482, 424/456, 476, 494, 496, 497, 498

[56] References Cited

U.S. PATENT DOCUMENTS

| | | | |
|---|---|---|---|
| 4,499,103 | 2/1985 | de Solms | 514/365 |
| 4,560,554 | 12/1985 | Kubo et al. | 424/71 |
| 4,767,627 | 8/1988 | Caldwell et al. | 424/426 |

*Primary Examiner*—Thurman K. Page
*Attorney, Agent, or Firm*—Millen, White & Zelano

[57] ABSTRACT

The present invention relates to a novel pharmaceutical composition comprising N-acetyl cysteine, wherein the composition releases N-acetyl cysteine in accordance with the United States Pharmacopea Standards (USP XXI, apparatus 2, 50 rpm) in an artificial gast-ric juice having pH 1.2 to an extent of less than 30% after 1 hr of exposure, and to less than 45% after 2 hrs of exposure, that it releases N-acetyl cysteine in accordance with the same standard in a phosphate buffer having pH 6.8 after 1 hr (3 hrs of total exposure) of at least 30%, and at most 100%, and in the same phosphate buffer of pH 6.8 after 5 hrs (7 hrs of total exposure) of at least 90%. The invention further comprises a method for treating symptoms as well as a method of preparing the composition.

17 Claims, 6 Drawing Sheets

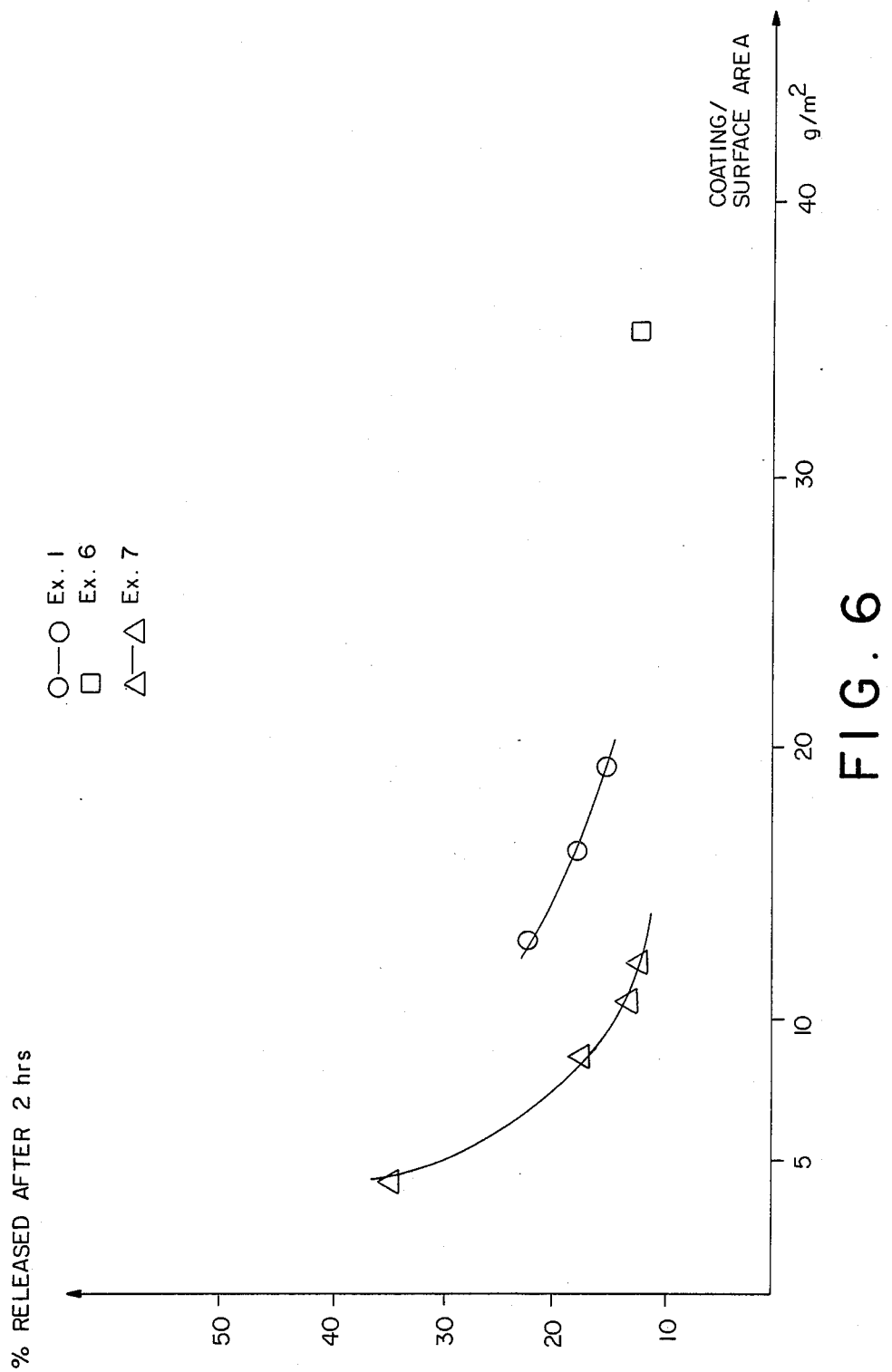

PHARMACEUTICAL DOSAGE WITH CORE OF N-ACETYL CYSTEIN

BACKGROUND OF THE INVENTION

Technical field

The present invention relates to a novel pharmaceutical composition comprising N-acetyl cysteine as active component.

N-Acetyl cysteine is used to dissolve or at least reduce the viscosity of mucous as produced in the breath ways, and including not only the lung tree but all the upper air ways including the cavities in the forehead and the cheeks, to prevent or treat sinuitis, to thereby eliminate or reduce the sympthoms of virus infections causing rinitis, bronchitis and other respiratory tract congestion. Acetyl cysteine will also be used as a scavenger to prevent cell death due to free radicals, and to prevent nitrate intolerance following chronic treatment with nitroglycerine and sustained release nitrate formulations.

N-Acetyl cysteine has hitherto been administered in the form of an effervescent composition which is dissolved in water by a carbon dioxide generating system prior to administration, or in the form of granules which are dissolved in water prior to use, or in the form of a matrix tablet comprising a skeleton of an insoluble polymer, which tablet leaks out N-acetyl cysteine into both the gastric and intestinal juices.

N-Acetyl cysteine has few reported side effects except an irritating effect on the mucous membrane in the stomach. It also has an extremely bad taste which per se creates a great problem in administering it.

The problem of the effervescent tablet composition containing N-acetyl cysteine, which presently is on the market, is that it has a very rapid onset of N-acetyl cysteine release. Thus, the effervescent composition, as well as the granulate present on the market, achieves a maximum blood plasma level within 1 hr from administration. The matrix formulation shows such a maximum point at 2-2.5 hrs after administration.

The object of the present invention is to obtain a pharmaceutical composition comprising N-acetyl cysteine and which composition has an improved bioavailability of N-acetyl cysteine.

SUMMARY OF THE PRESENT INVENTION

It has now very surprisingly been determined that one can increase the bioavailability of N-acetyl cysteine by administering it in the form of a composition which releases N-acetyl cysteine in accordance with United States Pharmacopea Standards (USP XXI, apparatus 2, 50 rmp) in an artificial gastric juice having pH 1.2 at the rate of less than 30% after 1 hr of exposure, and less than 45% after 2 hrs of exposure, and which releases N-acetyl cysteine in accordance with the same standard in a phosphate buffer having pH 6.8 at the rate of at least 30% after 1 hr (3 hrs of total exposure) of at and at least 90% after 5 hrs (7 hrs of total exposure).

BRIEF DESCRIPTION OF THE DRAWINGS

In the accompanying drawings,

FIGS. 5 and 6 are release patterns of compositions of this invention in 0.1 NHCl.

Figure 1:
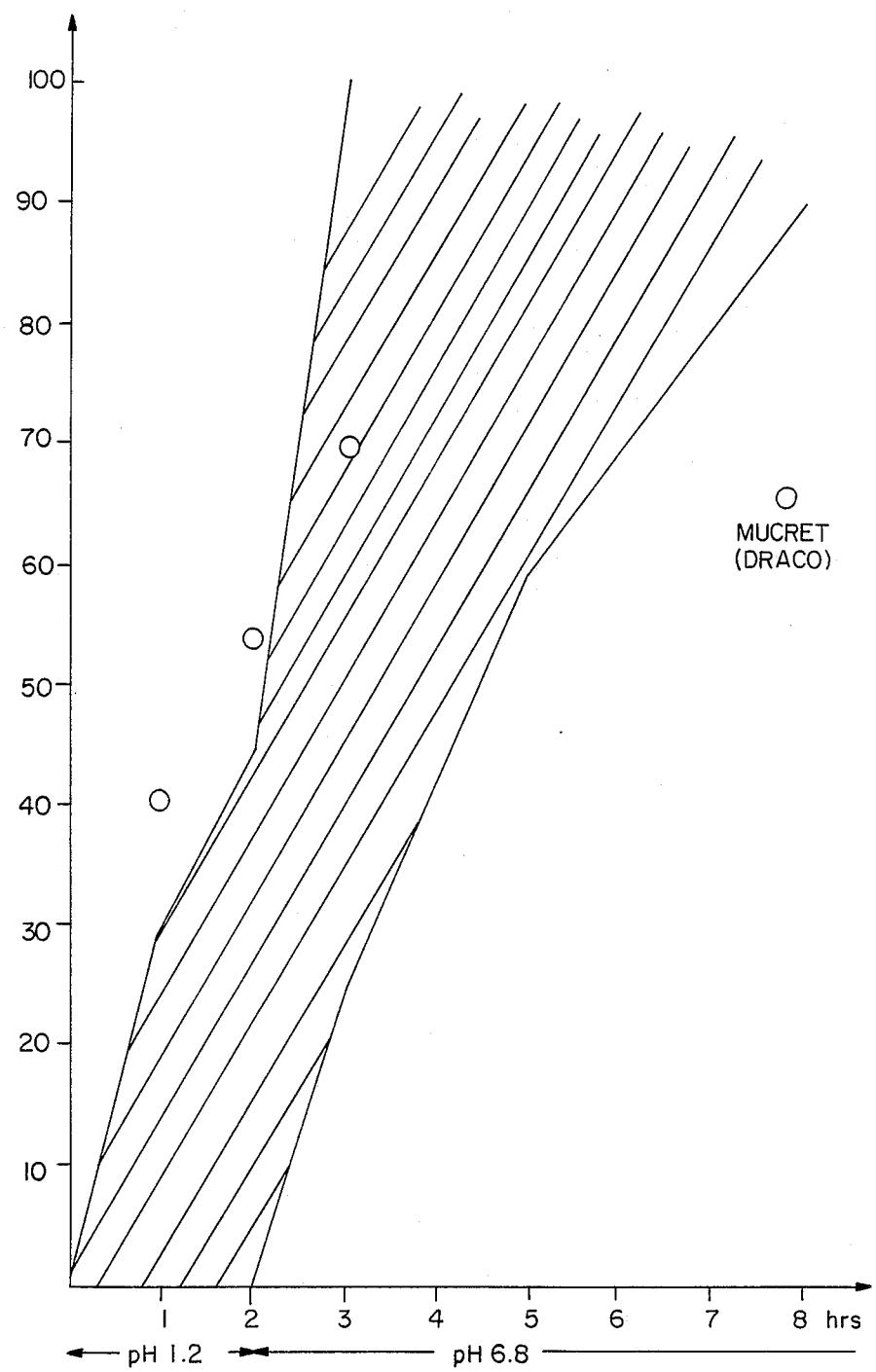
FIGS. 1-4 are comparisons of the release pattern of a composition of this invention and of a prior art product.

Further characteristics are evident from the accompanying claims.

The above release profile can be achieved using a composition with gastric acid resistant release properties, and retarded release properties in the intestinal fluid.

Such compositions have a core e.g., tablets, pills and granules which is coated with a gastric acid resistant polymer, such as an anionic polymer which is soluble in an aqueous solution having a pH of above 5.0.

Anionic polymers suitable coating the N-acetyl cysteine containing tablets, pills and granules are hydroxypropyl methyl cellulose phtalate (HP 50, HP 55), cellulose acetate phtalate, EUDRAGIT L, EUDRAGIT S (methyl methacrylate methylesters containing carboxylic acid groups), and polyvinyl acetate phtalate, and shellack.

The coating of anionic polymer can contain a plasticizer, such as cetanol, stearic acid and others.

It has now surprisingly turned out that the bioavailability of N-acetyl cysteine is radically increased using the present profile and compositions. Thus the bioavailability increases with 15-40% in relation to the compositions known and present on the market, as will be evident from below.

The Standard used to determine the release of N-acetyl cysteine and to define the present invention is U.S. Pharmacopea Standards (USP XXI, apparatus 2, 50 rpm), employing a stirring rate of 50 rpm.

The artificial gastric juice used has a pH of 1.2 and consists in accordance with said standard of 175 mls of concentrated HCl (35%) and 50 g of NaCl, diluted to 25000 mls using distilled water.

The phosphate buffer having a pH of 6.8 used in accordance with the same standard consist of 475.15 g of $Na_3PO_4 \times 12H_2O$ and 168 mls of conc. HCl, diluted to 25000 mls using distilled water.

The invention will be described more in detail in the following with reference to the Examples given, without however being restricted thereto.

EXAMPLE 1

Particulate N-acetyl cysteine, 80.0 kgs, was coated in a production line (fluid bed, closed cycle) with cetanol, 3.2 kgs (4%) in order to keep it free flowing, in accordance with SE-A-8700136-8 and to form aggregates of N-acetyl cysteine of the size 0.5-1.5 mm. 500 g of this thus cetanol coated product were then coated in the laboratory in a fluidized bed coater with a coating consisting of 3.5 g of cetanol and 64.5 g of hydroxypropyl methyl cellulose phtalate (HP 55) to give a coated granulate substantially spherical in form and 0.5-1.5 mm in size.

The active surface area of this granulate thus obtained was 4 $m^2$ per 500 g, which equates to 5 g of the first cetanol coating per $m^2$ and 17 g of the second, cetanol-containing anionic polymer coating per $m^2$.

In this Example 4% by weight of cetanol was used to coat the crystalline parties of the N-acetyl cysteine in a first coating. However, 2-15% by weight can be employed and the cetanol can be exchanged for fats, fatty acids, and fatty alcohols having 14-20 carbon atoms, such as stearic acid, stearic alcohol, hydrogenized castor oil, Na-stearylfumarate, Precirol ® (mono, di and triesters of palmitinic and stearic acid with glycerine).

EXAMPLES 2 TO 5

In accordance with Example 1 above four different N-acetyl cysteine compositions were produced in the laboratory in which the weight of the first inner coating of cetanol was varied to be 2% (Ex. 2), 4% (Ex. 3), 6% (Ex. 4), and 10% (Ex. 5), respectively.

EXAMPLE 6

In accordance with Example 1 500 g of the crystalline N-acetyl cysteine was first coated with 4% of cetanol, and the resulting granulates were coated with a mixture of 6.0 g of cetanol and 114.0 g of hydroxy propyl methyl cellulose phtalate (HP 55).

EXAMPLE 7

In accordance with Example 1 a granulate was prepared whereby also the second step was carried out in a production line. 7.58 kgs of hydroxypropyl methyl cellulose phtalate (HP 55) and up to 420 g of cetanol were used to coat 80 kgs of N-acetyl cysteine primarily granules. The thus-produced N-acetyl cysteine granulate had a total surface area of 592 m².

A number of tests and release profiles are described below with reference to the accompanying Figures, and the Tables hereinafter.

FIG. 1 enclosed shows the release profile of the compositions of the present invention, which compositions exhibit an increased bioavailability. As a comparison, the release of N-acetyl cysteine from a matrix tablet (MUCRET, Draco, Lund, SE) is shown (open rings).

Figure 2:
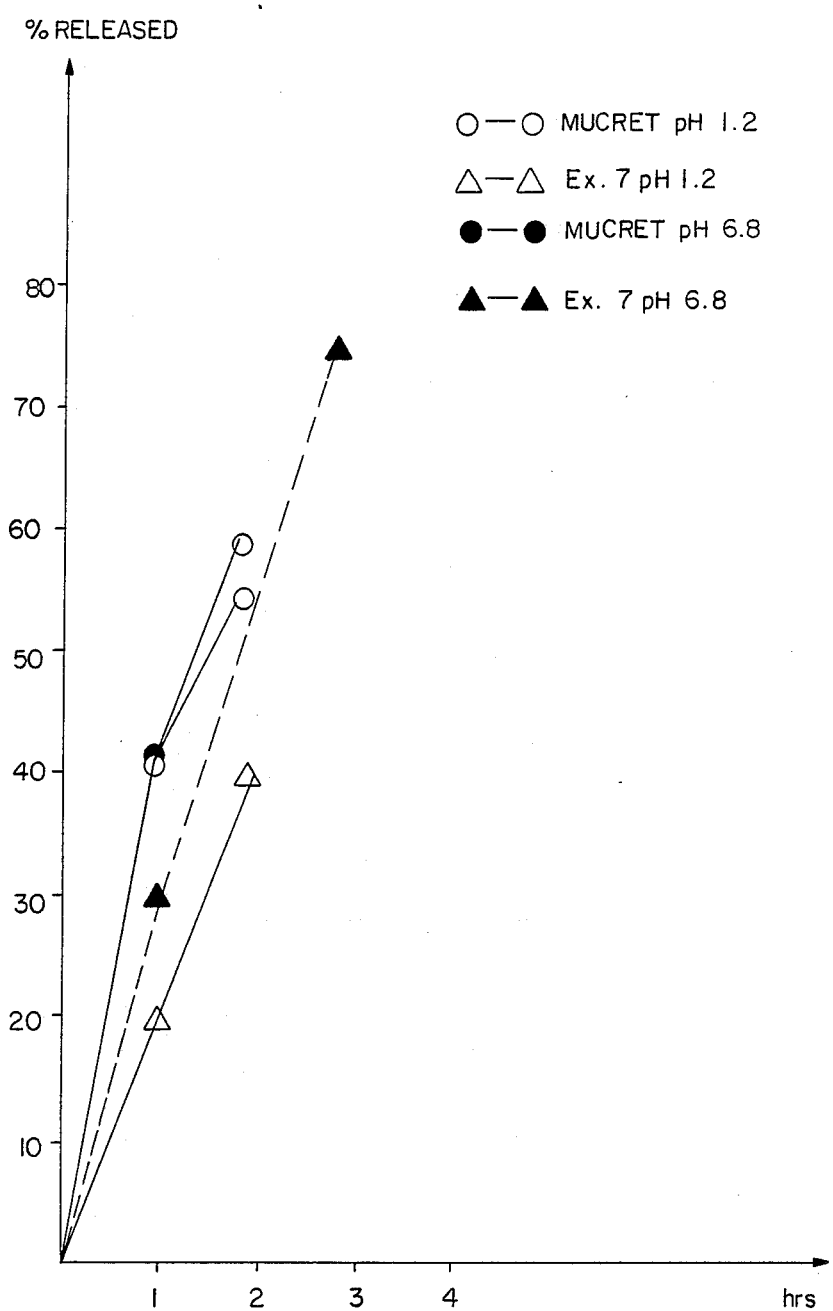

FIG. 2 is a comparison of the release profile of N-acetyl cysteine compared to the composition of Ex. 7 of the present invention and the matrix tablet (MUCRET) in pH 1.2 and pH 6.8 (no pre-exposure in pH 1.2), respectively.

Figure 3:
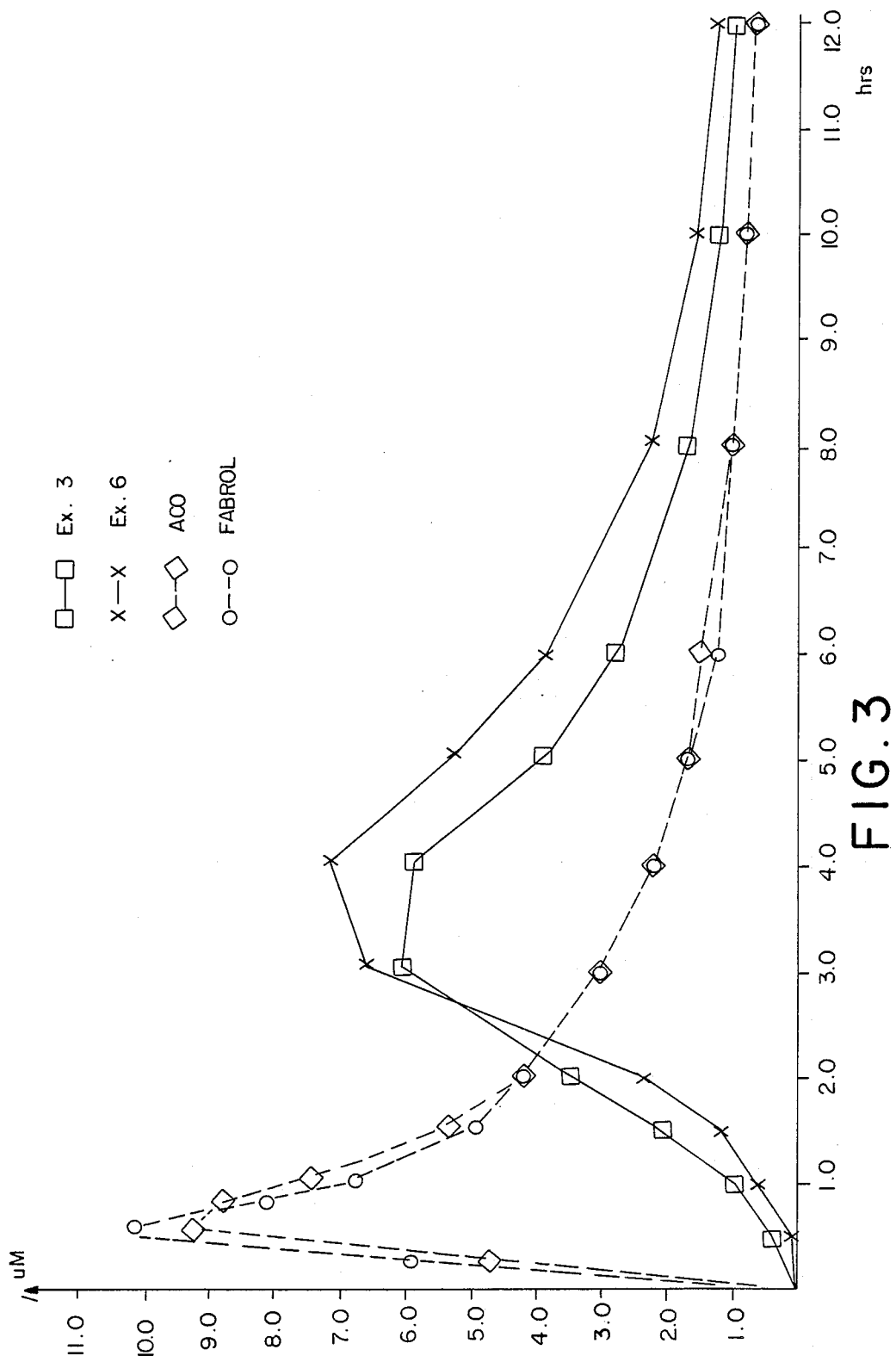

FIG. 3 is a single dose comparison in vivo between compositions of the present invention, viz., Ex. 3 and Ex. 6, and two commercial products, viz., an effervescent tablet (ACO) and granules (FABROL) the two latter compositions being dissolved in water prior to administration, whereby all compositions were administered in an amount which provided 400 mg of N-acetyl cysteine; the graph shows. The mean plasma concentration versus time after administration.

Figure 4:
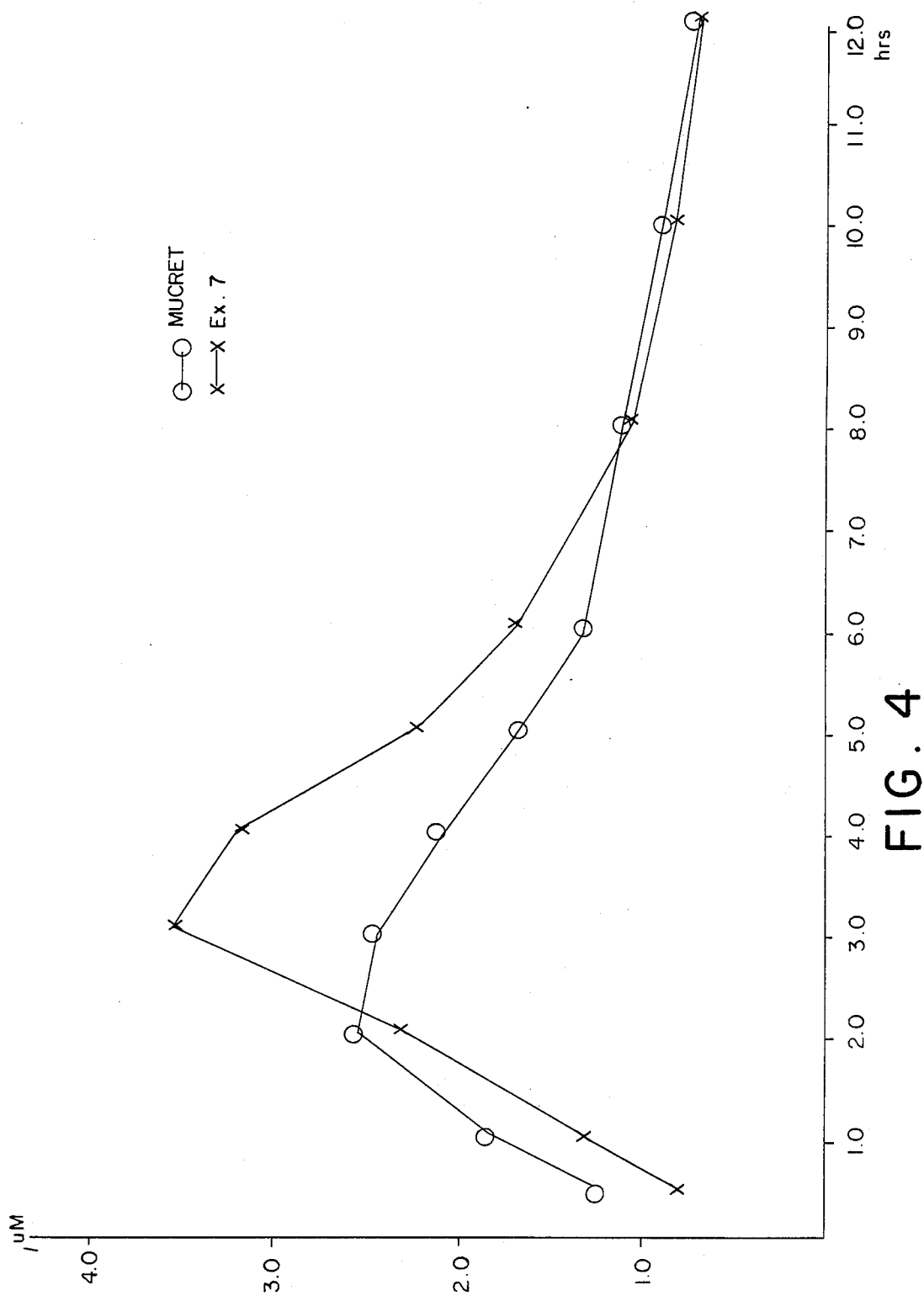

FIG. 4 is a similar single dose, in vivo comparison between the release profile of a composition of the present invention, viz., Ex. 7, and the matrix tablet (MUCRET), whereby N-acetyl cysteine being administered in an amount of 300 mg.

Figure 5:
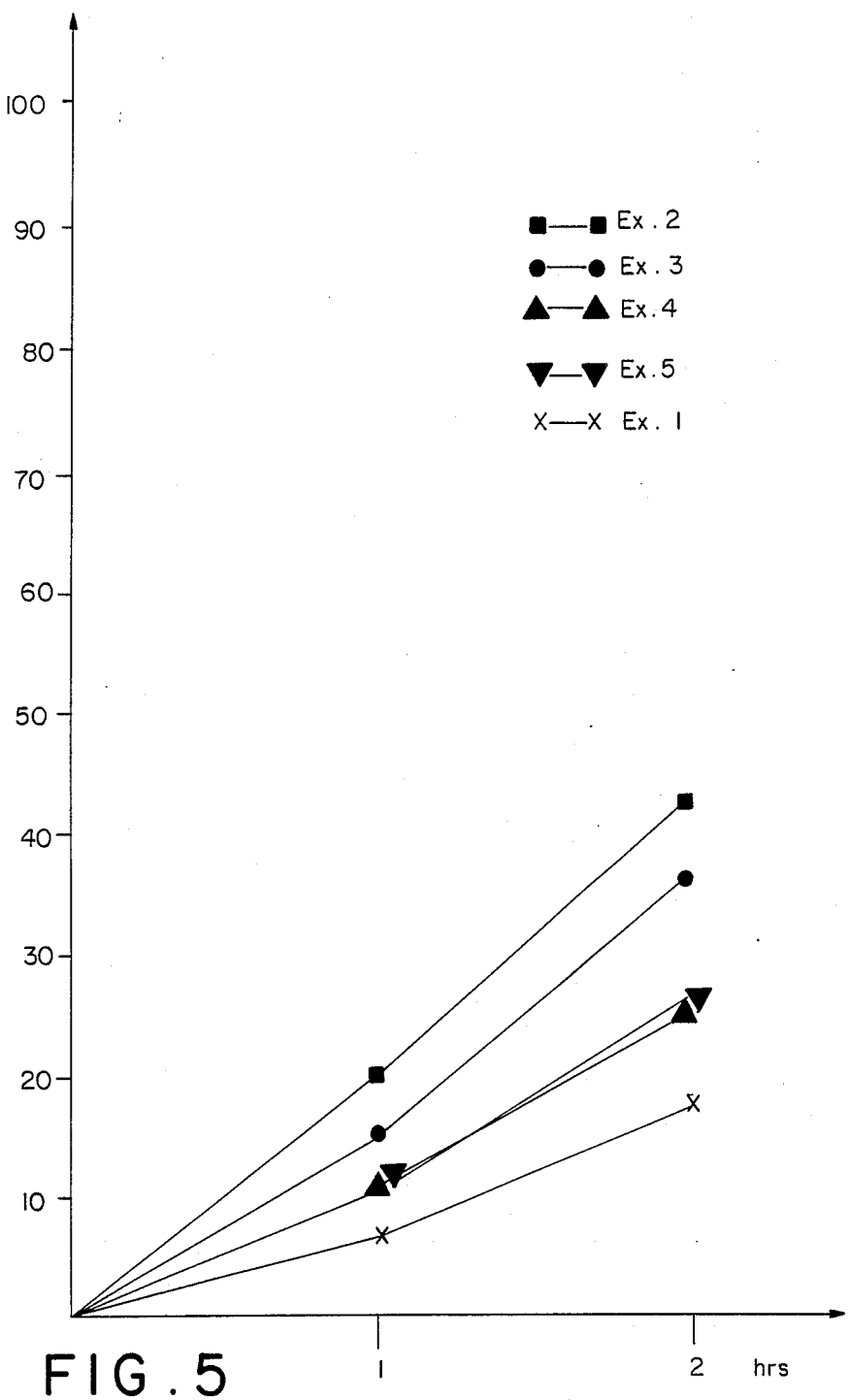

FIG. 5 shows the release profile of N-acetyl cysteine from the different compositions of Examples 1 to 5 in 0.1 M HCl.

FIG. 6 shows the release of N-acetyl cysteine of two compositions of Ex. 1, one of which (Ex. 7) was manufactured on a production scale. The graph shows the release after 2 hrs in 0.1 M HCl.

The present invention was compared in an in vivo study with a matrix tablet (MUCRET). Table 1 below shows the plasma concentration of N-acetyl cysteine in 10 patients after administration of 300 mg of N-acetyl cysteine one of the respective composition. The bioavailability of the composition of Ex. 1 of the invention is given in relative terms compared to the bioavailability of the matrix tablet.

TABLE 1

Individual N-acetyl cysteine concentrations (μM) and relative bioavailability (%) data after administration of 300 mg N-acetyl cysteine

| Subject No. | Matrix tablet | Ex. 7 of the present invention | |
|---|---|---|---|
| | | conc. | bioavailability (%) |
| 1 | 23.94 | 19.80 | 82.7 |
| 2 | 15.78 | 16.83 | 106.7 |
| 3 | 17.06 | 15.89 | 93.1 |
| 4 | 11.21 | 19.94 | 177.9 |
| 5 | 16.65 | 18.25 | 109.6 |
| 6 | 14.14 | 20.10 | 142.1 |
| 7 | 20.21 | 19.08 | 92.6 |
| 8 | 17.79 | 17.50 | 98.4 |
| 9 | 22.77 | 22.13 | 97.2 |
| 10 | 22.81 | 26.54 | 116.4 |
| 11 | 10.24 | 18.36 | 179.3 |
| 12 | 15.72 | 16.41 | 104.4 |
| Mean | 17.39 | 19.24 | 116.7 |

In another in vivo study a composition of the present invention, viz., Ex. 1 and Ex. 6, was compared with an effervescent tablet (ACO) and a granulate (FABROL) the two latter being administered as aqueous solutions. Table 2 gives the results from this test as plasma concentration, and the bioavailability relative the effervescent tablet.

TABLE 2

| Subject No. | ACO c.(1) | FABROL c. | FABROL BA(2) | Ex. 3 c. | Ex. 3 BA | Ex. 6 c. | Ex. 6 BA |
|---|---|---|---|---|---|---|---|
| 1 | 40.2 | 40.6 | 101.1 | 64.2 | 159.9 | 48.6 | 121.1 |
| 2 | 31.3 | 37.6 | 120.0 | 44.7 | 142.7 | 38.5 | 122.9 |
| 3 | 51.9 | 62.5 | 120.4 | 65.2 | 125.6 | 65.0 | 125.1 |
| 4 | 34.4 | 20.9 | 60.8 | 45.6 | 132.7 | 24.5 | 71.2 |
| 5 | 21.8 | 25.4 | 116.9 | 30.4 | 139.7 | 32.1 | 147.5 |
| 6 | 37.8 | 22.7 | 60.0 | 46.0 | 121.8 | 44.0 | 116.4 |
| 7 | 29.6 | 24.0 | 80.8 | 18.7 | 63.0 | 27.9 | 94.0 |
| 8 | 21.7 | 24.6 | 113.6 | 22.7 | 104.6 | 48.0 | 221.4 |
| 9 | 42.6 | 46.7 | 109.4 | 41.7 | 97.7 | 70.9 | 166.2 |
| 10 | 28.3 | 37.6 | 132.7 | 22.6 | 79.8 | 37.5 | 132.5 |
| 11 | 25.6 | 25.8 | 100.6 | 23.9 | 93.4 | 67.9 | 265.1 |
| 12 | 54.5 | 45.4 | 83.4 | 44.0 | 80.4 | 36.3 | 66.6 |
| Mean | 35.0 | 34.5 | 99.8 | 39.1 | 111.8 | 45.1 | 137.5 |

(1)c. means concentration measures in μM.H of N-acetyl cysteine in blood plasma
(2)BA means relative bioavailability Table 3 shows the release of N-acetyl cysteine in vitro from compositions of Ex. 3 and Ex. 6 at pH 1.2 and 6.8.

TABLE 3

In vitro dissolution rate of N-acetyl cysteine capsules of Ex. 1 and Ex. 6

| | pH 1.2 | | pH 6.8 | |
|---|---|---|---|---|
| Time | Ex. 3 | Ex. 6 | Ex. 3 | Ex. 6 |
| 1 hr | 13% | 5% | 66% | 61% |
| 2 hrs | 27% | 12% | 89% | 84% |

As evident from the drawings the release profile of the present invention is quite different from those of commercial products. Further, it is evident that the present invention gives a higher bioavailability of N-acetyl cysteine than do the products presently on the market.

As evident from FIG. 5 the inner coating of cetanol has some influence on the release rate of the N-acetyl cysteine, besides permitting coating in a fluidized bed, as it improves resistance to gastric acid release of the N-acetyl cysteine.

Using the compositions of this invention, the local irritating effect on the mucous membrane in the stomach will also be eliminated, as virtually no release of N-acetyl cysteine takes place in the ventricle.

The in the form of composition can be present as a tablet, pill or in the form of granules. When present as granules single doses of, 300-600 each are normally packed in soft or hard capsules, or in Sachet bags, whereby 2000-3000 granules having a size of generally 0.5-1.5 mm are present in a so called multiple-unit-dose. If the N-acetyl cysteine composition is administered as a multiple-unit-dose formulation in a gelatine capsule, the capsule as such will dissolve in the stomach, and the stomach will then function as a depot which slowly releases granules to the intestinal tract, where the coating of anionic polymer is dissolved and the N-acetyl cysteine is released from the core.

When the N-acetyl cysteine composition is present in the form of a tablet, commonly known tablet excipients are present, such as different types of starches, microcrystalline cellulose, lubricating agents, and other inert tabletting ingredients including taste and flavor providing agents. The tablets are punched in a common way to contain 200-600 mg of N-acetyl cysteine.

What is claimed is:

1. A solid pharmaceutical composition adapted for oral ingestion, comprising a core of N-acetyl cysteine whose surfaces have a hydrophobic coating thereon, which core is coated with an anionic polymer which is soluble in an aqueous solution having a pH of above 5.0 and which composition releases N-acetyl cysteine in accordance with United States Pharmacopea Standards (USP XXI, apparatus 2, 50 rpm) in an artificial gastric juice having pH 1.2 at the rate of less than 30% after 1 hr of exposure, and less than 45% after 2 hrs of exposure, and releases N-acetyl cysteine in accordance with the same standard in a phosphate buffer having pH 6.8 at the rate of at least 30% after 1 hr (3 hrs of total exposure) at least 90% after 5 hrs (7 hrs of total exposure).

2. Pharmaceutical composition according to claim 1, in the form of granules.

3. Pharmaceutical composition according to claim 1, wherein the granules are in a gelatin capsule.

4. Pharmaceutical composition according to claim 3, wherein the anionic polymer is hydroxypropyl methyl cellulose phtalate.

5. Pharmaceutical composition according to claim 1, wherein the core is particulate N-acetyl cysteine coated with 2-15% by weight of cetanol.

6. Pharmaceutical composition according to claim 1, wherein the anionic polymer is present in an amount of 5 to 40 g per $m^2$ of core surface.

7. Method for treating symptoms of excessive mucous secretion, preventing adverse effects of free radicals, and/or preventing nitrate intolerance by administering N-acetyl cysteine, wherein a thera-peutically active amount of a pharmaceutical composition of claim 1, is administered.

8. Method of manufacturing a pharmaceutical composition according to claim 1, which comprises the steps of fluidized bed coating the surfaces of particulate N-acetyl cysteine with a hydrophobic coating to form granules which are then coated with a polymer which is soluble in an aqueous solution having a pH of above 5.0.

9. Pharmaceutical composition according to claim 1, wherein the anionic polymer is hydroxypropyl methyl cellulose phthalate, present in an amount of 5 to 40 g per $m^2$ of core surface.

10. Pharmaceutical composition according to claim 9, wherein the core contains 2-15% by weight of cetanol.

11. Pharmaceutical composition according to claim 10, in the form of granules.

12. Pharmaceutical composition according to claim 11, wherein the granules are in a gelatin capsule.

13. A method for increasing the bioavailability of N-acetyl cysteine administered orally to treat symptoms of excessive mucous secretion, to prevent the adverse effects of free radicals, or prevent nitrate intolerance, which comprises administering the N-acetyl cysteine as a pharmaceutical composition of claim 1.

14. A method for increasing the bioavailability of N-acetyl cysteine administered orally to treat symptoms of excessive mucous secretion, to prevent the adverse effects of free radicals, or prevent nitrate intolerance, which comprises administering the N-acetyl cysteine as a pharmaceutical composition of claim 9.

15. A method for increasing the bioavailability of N-acetyl cysteine administered orally to treat symptoms of excessive mucous secretion, to prevent the adverse effects of free radicals, or prevent nitrate intolerance, which comprises administering the N-acetyl cysteine as a pharmaceutical composition of claim 10.

16. A method for increasing the bioavailability of N-acetyl cysteine administered orally to treat symptoms of excessive mucous secretion, to prevent the adverse effects of free radicals, or prevent nitrate intolerance, which comprises administering the N-acetyl cysteine as a pharmaceutical composition of claim 11.

17. The method according to claim 8, wherein the surfaces of the N-acetyl cysteine are coated with 2-15% by weight of cetanol.

* * * * *